US009598442B2

(12) United States Patent
Savonnet et al.

(10) Patent No.: US 9,598,442 B2
(45) Date of Patent: Mar. 21, 2017

(54) CRYSTALLIZED HYBRID SOLID HAVING A THREE-DIMENSIONAL DMOF-1-N₃ ORGANIC-INORGANIC MATRIX AND METHOD FOR PREPARING THE SAME

(75) Inventors: Marie Savonnet, Lyons (FR); David Farrusseng, Belmont d'Azegues (FR); Catherine Pinel, Lyons (FR); Delphine Bazer-Bachi, Saint-Genis-Laval (FR); Nicolas Bats, Saint Symphorien d'Ozon (FR); Vincent Lecocq, Orlienas (FR)

(73) Assignees: IFP ENERGIES NOUVELLES, Rueil-Malmaison (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 945 days.

(21) Appl. No.: 13/496,308

(22) PCT Filed: Sep. 3, 2010

(86) PCT No.: PCT/FR2010/000603
§ 371 (c)(1),
(2), (4) Date: Jul. 27, 2012

(87) PCT Pub. No.: WO2011/033185
PCT Pub. Date: Mar. 24, 2011

(65) Prior Publication Data
US 2012/0283435 A1  Nov. 8, 2012

(30) Foreign Application Priority Data
Sep. 18, 2009 (FR) ..................................... 09 04521

(51) Int. Cl.
*C07D 487/08* (2006.01)
*C07F 3/00* (2006.01)

(52) U.S. Cl.
CPC ................................... *C07F 3/003* (2013.01)

(58) Field of Classification Search
CPC ...................................................... C07D 487/08
USPC .......................................................... 544/350
See application file for complete search history.

(56) References Cited

PUBLICATIONS

Dybtsev, D. N. et al., "Rigid and Flexible: A Highly Porous Metal-Organic Framework with Unusual Guest-Dependent Dynamic Behavior," Angew. Chem. Int. Ed., 2004, vol. 43, pp. 5033-5036.
International Search Report for PCT/FR2010/000603 dated Nov. 16, 2010.
Lee, J. Y. et al., "Microporous metal-organic Frameworks with High Gas Sorption and Separation Capacity," Advanced Functional Materials, 2007, vol. 17, pp. 1255-1262.
Mautner, F. A. et al., "1D and 2D Systems Derived from Polynuclear [ML(N₃)₂]n (M=Zn(II) or Cd(II) and L is 2-Picoline-N-Oxide or 4-Methylpyrimidine)" Monatshefte Für Chemie, 2005, vol. 136, pp. 107-117.
Wang, Z. et al., "Accessing Postsynthetic Modification in a Series of Metal-Organic Frameworks and the Influence of Framework Topology on Reactivity," Inorganic Chemistry, 2009, vol. 48, No. 1, pp. 296-306.

*Primary Examiner* — Douglas M Willis
(74) *Attorney, Agent, or Firm* — Millen, White, Zelano and Branigan, P.C.

(57) ABSTRACT

A crystallized hybrid solid with an organic-inorganic matrix, of three-dimensional structure, containing an inorganic network of zinc-based metal centers connected to one another by organic ligands constituted by the entities —O₂C—C₆H₃—N₃—CO₂— and C₆H₁₂N₂. Said solid is called DMOF-1-N₃, and has Zn₂(—O₂C—C₆H₃—N₃—CO₂—)₂ (C₆H₁₂N₂) for its base pattern.

11 Claims, 1 Drawing Sheet

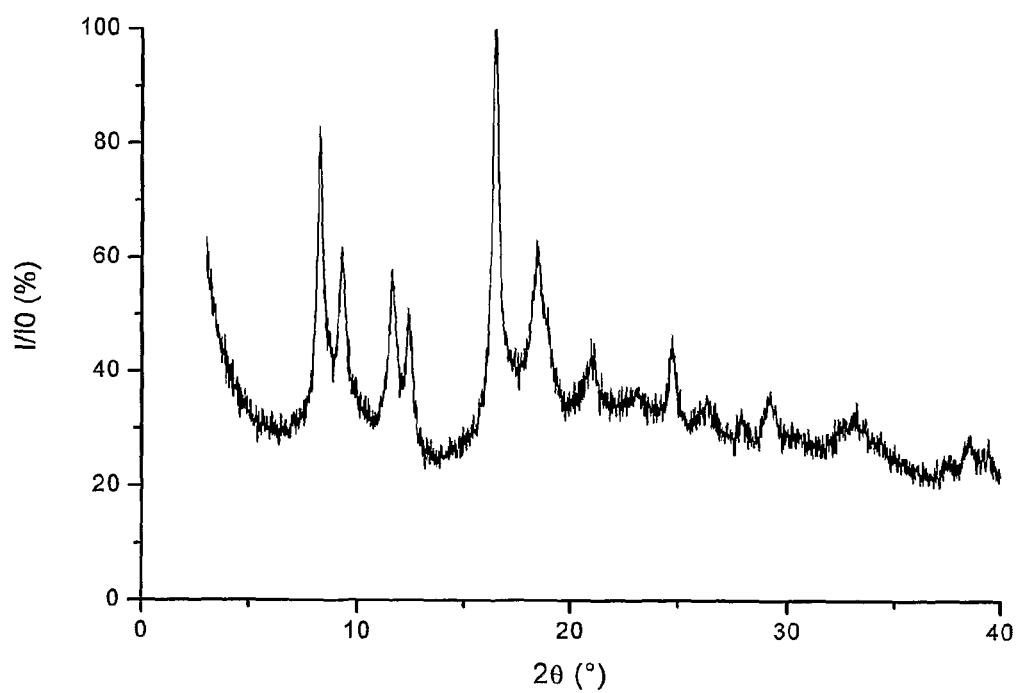

CRYSTALLIZED HYBRID SOLID HAVING A THREE-DIMENSIONAL DMOF-1-N₃ ORGANIC-INORGANIC MATRIX AND METHOD FOR PREPARING THE SAME

TECHNICAL FIELD OF THE INVENTION

This invention relates to a new crystallized hybrid solid with an organic-inorganic matrix, of three-dimensional structure, and to its process for preparation starting from the DMOF-1-NH$_2$ crystallized hybrid solid with an organic-inorganic matrix that is already described in the literature. Said new solid, object of this invention, carries one azide group and is called DMOF-1-N$_3$ in the description below. Said DMOF-1-N$_3$ solid has a crystalline structure that is identical to that of the DMOF-1-N$_2$ solid with which it is obtained by a post-synthesis functionalization method. Said DMOF-1-N$_3$ solid is advantageously used in applications as catalyst or adsorbent or else as an intermediate product for obtaining functionalized crystallized hybrid solids with an organic-inorganic matrix.

STATE OF THE ART

The modification of materials by functionalization is a stage that is often necessary for the production of solids that have the properties that are suitable for a given application. Actually, it may be desirable to improve the physico-chemical properties of a material by modifying its surface, for example, so that the new properties that are obtained after modifications are more suitable for separation or catalysis applications.

One of the means that is commonly used for modifying the surface of a material consists in reacting the functional groups that are initially present on its surface by entities that have the groups that are desired for the application being considered. The groups that are present on the surface of a material can be hydroxyl groups (—OH) or any other group (—NH$_2$ or —NH— amine, for example) that it is desired to modify so as to orient the chemical reactivity of the surface of the material. The reagents that are used will have the functionalities that are necessary for reacting with the groups that are initially present on the surface of the material, and the result of the reaction will be a new chemical group that has the desired reactivity. An example of such a transformation consists in reacting the hydroxyl groups of the surface of a silica by a silane that carries one amine group (D. Brunel, *Microporous and Mesoporous Materials*, 1999, 27, 329-344). Thus, the hydroxyl group is transformed into an amine group that is more capable of catalyzing basic reactions or of collecting CO$_2$, for example. This methodology can be applied to any material that initially has reactive groups. These materials can be oxides, zeolites, or else organic/inorganic hybrid materials, also called coordination polymers.

These coordination polymers, of which the first were described in the 1960's, are the subject of a growing number of publications. Actually, the effervescence around these materials made it possible to achieve an advanced structural diversity in a short time (Férey, G., l'actualité chimique [Chemical Issues], January 2007, No. 304). Conceptually, the porous hybrid solids with an organic-inorganic mixed matrix are quite similar to porous solids with inorganic skeletons. Like the latter, they combine chemical entities by giving rise to porosity. The primary difference resides in the nature of these entities. This difference is particularly advantageous and is at the origin of all of the versatility of this category of hybrid solids. Actually, the pore size becomes, by using organic ligands, adjustable by means of the length of the carbon-containing chain of said organic ligands. The framework, which in the case of inorganic porous materials can only accept some elements (Si, Al, Ge, Ga, optionally Zn), can, in this case, collect all of the cations except for the alkalines. For the preparation of these hybrid materials, no specific structuring agent is required; the solvent performs this action by itself.

It therefore clearly appears that this family of hybrid materials makes possible a multiplicity of structures and consequently comprises solids that are finely adapted to the applications that are intended for them.

The coordination polymers comprise at least two elements that are called connectors and ligands whose orientation and whose number of connecting sites are decisive in the structure of the hybrid material. An immense variety of hybrid materials is born, as was already specified, from the diversity of these ligands and connectors.

Ligand refers to the organic part of the hybrid material. These ligands are, most often, di- or tri-carboxylates or derivatives of pyridine. Some organic ligands that are frequently encountered are shown below: bdc=benzene-1,4-dicarboxylate, btc=benzene-1,3,5-tricarboxylate, ndc=naphthalene-2,6-dicarboxylate, bpy=4,4'-bipyridine, hfipbb=4,4'-(hexafluoroisopropylidene)-bisbenzoate, cyclam=1,4,8,11-tetraazacyclotetradecane.

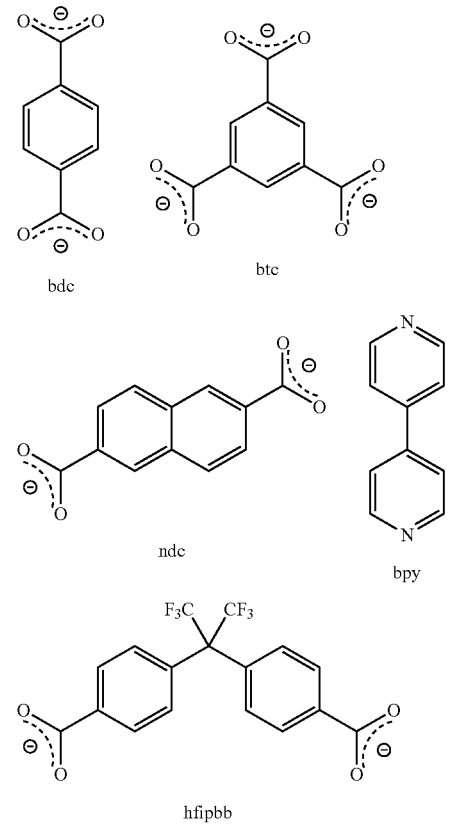

-continued

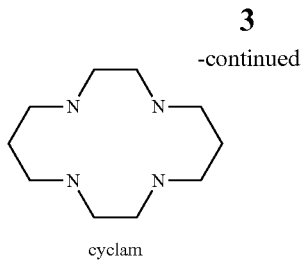

cyclam

Connector refers to the inorganic entity of the hybrid material. It may involve a single cation, a dimer, trimer or tetramer, or else a chain or a plane.

Within the framework of this invention, the ligands that are used are 2-amino-terephthalic acid ($NH_2$-bdc) and 1,4-diazabicyclo[2.2.2]octane (DABCO). The inorganic entity that performs the role of connector is zinc.

The teams of Yaghi and Férey thus described a large number of new hybrid materials (series of MOF—"Metal Organic Framework"—and series of MIL—"Materials of l'Institut Lavoisier [Lavoisier Institute]"—respectively). Numerous other teams followed this path, and today, the number of new hybrid materials described is expanding rapidly. Most often, the purpose of the studies is to develop ordered structures, having extremely large pore volumes, good thermal stability, and adjustable chemical functionalities.

For example, Yaghi et al. describe a series of boron-based structures in the patent application U.S. 2006/0154807 and indicate their advantage in the field of gas storage. The patent U.S. Pat. No. 7,202,385 discloses a particularly complete summary of the structures that are described in the literature and perfectly illustrates the multitude of materials already existing as of this time.

The preparation of the organic-inorganic hybrid materials that have a reactive organic group (grafted MOF) can be implemented by two primary paths: the functionalization by self-assembly and the functionalization by post-modification. The functionalization by self-assembly is implemented by presenting an organic ligand that has the desired reactive group (graft) and an inorganic compound that has the role of connector. This method of functionalization is often difficult to implement because of problems linked to the solubilization and the reactivity of functionalized ligands. In particular, the ligands that carry an —OH, —COOH or —$NH_2$ group run the risk of interacting with the inorganic compound (connector) then leading to non-isostructural solids with non-grafted reference MOF. The functionalization by post-modification is an advantageous alternative method that does not have the limits of functionalization by self-assembly. The functionalization by post-modification consists in directly modifying the organic group of at least one type of ligand that is present in the MOF by a chemical reaction (grafting), more specifically in substituting the initial organic group by an organic group whose reactivity is preferred for a subsequent application. This method assumes the presence on the initial MOF of an organic group that is accessible and reactive for grafting. In literature, the organic-inorganic hybrid materials that carry a ligand with an —$NH_2$ amino group, such as DMOF-1-$NH_2$ (Z. Q. Wang; K. K. Tanabe, S. M. Cohen, *Inorganic Chemistry*, 2009, 48, 296-306), are described as good substrates for the grafting of numerous groups, in particular aldehydes, isocyanates, and acid anhydrides.

DESCRIPTION OF THE INVENTION

This invention has as its object a new crystallized hybrid solid with an organic-inorganic matrix that has a three-dimensional structure. This new solid is called DMOF-1-$N_3$. It contains an inorganic network of zinc-based metal centers that are connected to one another by organic ligands that consist of the —$O_2C$—$C_6H_3$—$N_3$—$CO_2$— and $C_6H_{12}N_2$ entities.

The DMOF-1-$N_3$ crystallized hybrid solid according to the invention has an X-ray diffraction diagram that includes at least the lines that are inscribed in Table 1. This diffraction diagram is obtained by radiocrystallographic analysis by means of a diffractometer by using the conventional powder method with K$\alpha$1 copper radiation ($\lambda$=1.5406 Å). Starting from the positions of diffraction peaks shown by the angle 2θ, the characteristic reticular equidistances $d_{hkl}$ of the sample are calculated by applying Bragg's equation. The measuring error $\Delta(d_{hkl})$ to $d_{hkl}$ is calculated using Bragg's equation based on the absolute error $\Delta(2\theta)$ that is assigned to the measurement of 2θ. An absolute error of $\Delta(2\theta)$ that is equal to ±0.02° is commonly allowed. The relative intensity $I/I_o$ assigned to each $d_{hkl}$ value is measured according to the height of the corresponding diffraction peak. The X-ray diffraction diagram of the DMOF-1-$N_3$ crystallized hybrid solid according to the invention comprises at least the lines with the values of $d_{hkl}$ given in Table 1. In the $d_{hkl}$ column, the mean values of the inter-reticular distances are indicated in angstroms (Å). Each of these values is to be affected by the measuring error $\Delta(d_{hkl})$ encompassed between ±0.3 Å and ±0.01 Å.

TABLE 1

Mean Values of $d_{hkl}$ and Relative Intensities Measured on an X-Ray Diffraction Diagram of the DMOF-1-$N_3$ Crystallized Hybrid Solid.

| 2 Thêta (°) | $d_{hkl}$ (Å) | $I/I_0$ |
|---|---|---|
| 8.152 | 10.837643 | F |
| 9.19 | 9.615264 | mf |
| 11.538 | 7.663371 | mf |
| 12.296 | 7.192531 | mf |
| 14.77 | 5.992845 | ff |
| 16.345 | 5.418821 | FF |
| 18.29 | 4.846741 | f |
| 18.44 | 4.807632 | ff |
| 18.782 | 4.720763 | f |
| 20.19 | 4.394638 | ff |
| 20.504 | 4.327992 | ff |
| 21.806 | 4.072553 | ff |
| 23.195 | 3.831685 | ff |
| 24.623 | 3.612547 | f |
| 24.737 | 3.596266 | ff |
| 24.996 | 3.559468 | ff |
| 25.978 | 3.427163 | ff |
| 26.086 | 3.413252 | ff |
| 26.333 | 3.381744 | ff |
| 27.609 | 3.228232 | ff |
| 27.813 | 3.205088 | ff |
| 29.029 | 3.0735 | f |
| 29.698 | 3.005821 | ff |
| 29.793 | 2.996423 | ff |
| 30.201 | 2.956894 | ff |
| 30.938 | 2.888069 | ff |
| 31.15 | 2.868907 | ff |
| 32.046 | 2.790679 | ff |
| 32.428 | 2.758663 | ff |
| 33.035 | 2.709411 | ff |
| 33.492 | 2.673413 | ff |
| 34.082 | 2.628514 | ff |
| 34.36 | 2.607855 | ff |
| 35.102 | 2.554457 | ff |
| 35.184 | 2.548681 | ff |
| 35.373 | 2.535482 | ff |
| 36.361 | 2.468819 | ff |
| 36.52 | 2.458421 | ff | where

TABLE 1-continued

Mean Values of $d_{hkl}$ and Relative Intensities Measured on an X-Ray Diffraction Diagram of the DMOF-1-$N_3$ Crystallized Hybrid Solid.

| 2 Thêta (°) | $d_{hkl}$ (Å) | I/I$_0$ |
|---|---|---|

FF = Very High;
F = High;
m = Medium;
mf = Medium Low;
f = Low; and
ff = Very Low.
The relative intensity I/I$_0$ is provided relative to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; and FF ≥ 85.

The DMOF-1-$N_3$ crystallized hybrid solid according to the invention has a crystalline structure with a base or topology that is characterized by its X-diffraction diagram provided by FIG. 1. The crystalline structure of the DMOF-1-$N_3$ crystallized hybrid solid according to the invention is identical to the one that is exhibited by the DMOF-1-$NH_2$ crystallized hybrid solid that is described in the literature (Z. Q. Wang; K. K. Tanabe, S. M. Cohen, *Inorganic Chemistry*, 2009, 48, 296-306), and from which said DMOF-1-$N_3$ solid is obtained, in accordance with the process for preparation described farther down in this description.

The DMOF-1-$N_3$ crystallized hybrid solid according to the invention is indexed in a quadratic system of the P4/m space group with, as mesh parameters, a=b=10.837 Å; c=9.614 Å, and alpha=beta=gamma=90°, with these definitions (quadratic system, space group and mesh parameters) being well known to one skilled in the art.

The DMOF-1-$N_3$ crystallized hybrid solid according to the invention has a three-dimensional structure in which the inorganic network that is formed by $Zn^{2+}$-cation-based metal centers that perform the role of connectors are linked together by deprotonated terephthalic ligands (—$O_2C$—$C_6H_3$—$N_3$—$CO_2$—) that carry an $N_3$ azide group on the aromatic cycle and ligands that consist of 1,4-diazabicyclo[2.2.2]octane (DABCO of empirical formula $C_6H_{12}N_2$). An essential characteristic of the DMOF-1-$N_3$ crystallized hybrid solid according to the invention resides in the presence of the azide group on the aromatic cycle of each of the deprotonated terephthalic ligands, more specifically called 2-azido-terephthalate ligands (denoted $N_3$-bdc). The structure that is obtained, identical to that of DMOF-1-$NH_2$, is three-dimensional. The zinc dimers are connected to one another by deprotonated terephthalic ligands that form square grids (by combination of 4 Zn dimers and 4 $N_3$-bdc ligands), which lead to a 3D structure by the superposition of these grids by the columns of DABCO ligands. Each Zn atom is therefore pentacoordinated: each zinc atom is surrounded by four oxygen atoms obtained from 4 $N_3$-bdc ligands that are located in equatorial position and a nitrogen atom that is obtained from a DABCO ligand that is located in apical position. An $N_3$-bdc ligand is connected to 4 zinc atoms. A DABCO ligand is connected to 2 zinc atoms. The $N_3$-bdc ligands occupy the equatorial positions while the DABCO ligands connect the zinc atoms in apical position.

The DMOF-1-$N_3$ crystallized hybrid solid according to the invention thus has a chemical composition that has $Zn_2$(—$O_2C$—$C_6H_3$—$N_3$—$CO_2$—)$_2$($C_6H_{12}N_2$) for its base pattern. This pattern is repeated n times, with the value of n based on the crystallinity of said solid.

The DMOF-1-$N_3$ crystallized hybrid solid according to the invention has also been characterized by Fourier Transform Infrared (FT-IR) spectroscopy and by $^1$H NMR in such a way as to verify the presence of the azide group on each of the terephthalate ligands. Thus, the spectrum that is obtained by FT-IR has a characteristic band of the azide group at 2123 cm$^{-1}$. The $^1$H-NMR analysis is implemented on a sample of said DMOF-1-$N_3$ hybrid solid according to the invention, after digestion and total dissolution of said sample in a DCl/$D_2O$/DMSO-$d_6$ deuterated mixture according to an operating mode described in the literature (Z. Q. Wang, S. M. Cohen, *Journal of the American Chemical Society*, 2007, 129, 12368-12369). The $^1$H-NMR analysis confirms the presence of the $N_3$ azide group on the aromatic cycle of the deprotonated terephthalic ligand: δ=7.74-7.85 ppm, m, 3H, ArH. The 3 protons leading to the detection of the multiplet correspond to the 3 protons carried by the aromatic cycle of the 2-azido-terephthalate ($N_3$-bdc) ligand.

This invention also has as its object a process for the preparation of the DMOF-1-$N_3$ crystallized hybrid solid. Said DMOF-1-$N_3$ solid is prepared from the DMOF-1-$NH_2$ crystallized hybrid solid that is described in the literature (Z. Q. Wang; K. K. Tanabe, S. M. Cohen, *Inorganic Chemistry*, 2009, 48, 296-306). Said DMOF-1-$NH_2$ solid has a three-dimensional structure with an inorganic network that is formed by $Zn^{2+}$-cation-based metal centers that perform the role of connectors linked together by deprotonated terephthalic ligands that carry an —$NH_2$ amine group on the aromatic cycle (denoted $NH_2$-bdc ligands) and ligands that consist of 1,4-diazabicyclo[2.2.2]octane (DABCO). A method for preparation of said DMOF-1-$NH_2$ solid is described in the literature (Z. Q. Wang; K. K. Tanabe, S. M. Cohen, *Inorganic Chemistry*, 2009, 48, 296-306. The process for preparation of the invention makes possible the substitution of the —$NH_2$ amine group that is present in the DMOF-1-$NH_2$ solid by the $N_3$ azide group. The process for preparation according to the invention comprises at least the following stages:

i/ Introduction, into a polar solvent S, of at least said DMOF-1-$NH_2$ crystallized hybrid solid, at least one organic compound Q that contains an $N_3$ azide group, and at least one intermediate reagent R that contains an $NO_2$ nitrite group in a proportion such that the reaction mixture has the following molar composition:

1 DMOF-1-$NH_2$:3-12 R:1-9 Q:100-400 S ii/ Reaction of said reaction mixture at a temperature of between 0 and 100° C. for a period of between 1 and 24 hours to obtain said DMOF-1-$N_3$ crystallized hybrid solid, iii/ Filtration, and then washing of said DMOF-1-$N_3$ crystallized hybrid solid, iv/ Drying of said DMOF-1-$N_3$ crystallized hybrid solid.

In accordance with said stage i) of said process for the preparation of the DMOF-1-$N_3$ crystallized hybrid solid according to the invention, said DMOF-1-$NH_2$ crystallized hybrid solid is dried in advance before being introduced into said polar solvent. The drying of said DMOF-1-$NH_2$ crystallized hybrid solid is advantageously implemented at a temperature of between 20 and 100° C. for a period of between 1 and 24 hours, very advantageously for a period of approximately 12 hours. The drying is done in air or under vacuum, in a preferred manner under vacuum.

In accordance with said stage i) of the process for preparation according to the invention, said organic compound Q that contains an $N_3$ azide group is advantageously selected from among trimethylsilyl azide (TMS-$N_3$, ($CH_3$)$_3$Si$N_3$), triflyl azide (Tf$N_3$, where Tf=$CF_3SO_2$), p-tosyl azide (Ts$N_3$ or 4-methylbenzenesulfonyl azide of formula $C_6H_4$($CH_3$)$SO_2N_3$), and sodium azide (Na$N_3$). In a preferred manner, said organic compound Q that contains an $N_3$ group is trimethylsilyl azide (TMS-$N_3$).

In accordance with said stage i) of the process for preparation according to the invention, said intermediate reagent R that contains an $NO_2$ nitrite group is advantageously selected from among alkaline reagents such as sodium nitrite ($NaNO_2$) and calcium nitrite ($Ca(NO_2)_2$), metal reagents, and alkoxy-type reagents such as tert-butyl-nitrite (tBuONO, $(CH_3)_3CONO$). In a very preferred manner, said intermediate reagent R that contains an $NO_2$ nitrite group is tert-butyl-nitrite (tBuONO). Said intermediate reagent R that contains an $NO_2$ nitrite group ensures the formation of a diazonium salt that next reacts with the organic compound Q.

The polar solvent S that is used in said stage i) of the process for preparation according to the invention is preferably volatile. It is very advantageously selected from among tetrahydrofuran (THF) and acetonitrile.

In accordance with said stage i) of the process for preparation according to the invention, the reaction mixture preferably has the following molar composition:

1 $DMOF-1-NH_2$:5-7 R:5-8 Q:100-200 S

Said reaction stage in accordance with said stage ii) of the process for preparation according to the invention is preferably implemented at a temperature of between 0 and 60° C., and even more preferably at ambient temperature. The reaction mixture is stirred using a magnetic stirrer. The reaction period is between 1 and 24 hours, preferably between 5 and 15 hours, and most often approximately 12 hours. The solid that is obtained at the end of said stage ii) is a $DMOF-1-N_3$ crystallized hybrid solid that has an X-ray diffraction diagram that includes at least the lines inscribed in Table 1.

According to said stage iii) of the process for preparation according to the invention, said $DMOF-1-N_3$ crystallized hybrid solid that is obtained at the end of said stage ii) is filtered and then washed with suitable solvents. The washing of said $DMOF-1-N_3$ solid is preferably implemented by a first washing sequence by means of polar solvents, for example THF, followed by a second washing sequence by means of volatile solvents, for example dichloromethane. The washing stage of said $DMOF-1-N_3$ crystallized hybrid solid is initiated, for example, by implementing 3 sequences of washing with THF followed by 3 sequences of washing with $CH_2Cl_2$ dichloromethane.

In accordance with said stage iv) of the process for preparation according to the invention, said $DMOF-1-N_3$ crystallized hybrid solid is dried. The drying is done in air or under vacuum between 20° C. and 100° C. In a preferred manner, the drying is done at ambient temperature under vacuum for a period that varies between 1 and 24 hours, most often approximately 12 hours.

In accordance with the process for preparation according to the invention, the DABCO ligands are non-reactive ligands: they do not compete with the $NH_2$-bdc ligands, and they do not react with said organic compound Q that contains said $N_3$ group.

The solid that is obtained at the end of stage iv) is identified as being the $DMOF-1-N_3$ crystallized hybrid solid according to the invention. The analyses that are implemented on the solid that is obtained at the end of the process for preparation according to the invention demonstrate the effectiveness of the treatment by post-modification. In particular, the analysis that is implemented on the $DMOF-1-N_3$ crystallized hybrid solid by XRD demonstrates that the treatment of functionalization by post-modification that makes it possible to substitute the —$NH_2$ amino group by the —$N_3$ azide group does not affect the structure and the crystallinity of the solid. The FT-IR analysis reveals the presence of the —$N_3$ azide group on each of the terephthalate ligands in the $DMOF-1-N_3$ solid. The $^1H$-NMR analysis confirms the presence of the —$N_3$ azide group on each of the terephthalate ligands in the $DMOF-1-N_3$ solid and makes it possible to estimate the rate of modification of the amino groups into $N_3$ azide groups. In accordance with the process for preparation according to the invention, this rate of modification is very high, i.e., at least equal to 95%, preferably at least equal to 98%. The rate of modification is calculated by quantifying the decrease in the relative area of the signals of aromatic protons of the $DMOF-1-NH_2$ form relative to those of the $DMOF-1-N_3$ form. The $^1H$-NMR spectrum of the $DMOF-1-N_3$ solid according to the invention has new signals that are linked to the appearance of an integral multiplet for 3 protons, which correspond to the 3 protons that are carried by the aromatic cycle of the 2-azido-terephthalate ($N_3$-bdc) ligand.

EXAMPLES

The $DMOF-1-NH_2$ and $DMOF-1-N_3$ crystallized hybrid solids that are obtained at the end of the implementation of the preparation protocols illustrated by the following Examples 1 and 2 have been analyzed by X-ray diffraction, by Fourier Transform Infrared (FT-IR) spectroscopy, and by nuclear magnetic resonance of hydrogen ($^1H$ NMR).

The X-ray diffraction diagrams are obtained by radiocrystallographic analysis by using the standard powder method by means of a Bruker D5005 diffractometer ($CuK\alpha_{1+2}$=0.15418 nm) that is equipped with a graphite curved rear monochromator and a scintillation detector. The analyses of the solids have been recorded with the Debye-Scherrer method from 3 to 80° (2θ) with a pitch of 0.02° for 8 seconds.

The infrared analyses are done using KBr pellets on a Bruker Vector 22 FT-IR device with a useful operating range of: 4,000-400 $cm^{-1}$.

The nuclear magnetic resonance spectra in solution are obtained using a Bruker Avance 250 NMR spectrometer (5.87 T, 250 MHz for 1H).

Example 1

Preparation of the $DMOF-1-NH_2$ Crystallized Hybrid Solid 0.781 g of $Zn(NO_3)_2.4H_2O$ zinc nitrate (3.00 mmol, Merck, 98.5%), and 0.554 g of $NH_2$-BDC 2-amino-1,4-benzenedicarboxylic acid (3.03 mmol, Alfa Aesar, 99%) are dissolved in 75 ml of dimethylformamide (DMF, Aldrich, 99.8%). 0.542 g of 1,4-diazabicyclo[2.2.2]octane DABCO (4.815 mmol, Aldrich, 98%) is next added to the solution. This addition is reflected by the immediate appearance of a white precipitate. The precipitate that is obtained is filtered on low-porosity sintered [sic] while the filtrate is recovered and diluted with 75 ml of DMF. The solution that consists of filtrate is next divided into 5 aliquots of 30 ml that are distributed into 5 stainless steel autoclaves (43 ml capacity) and heated from 35 to 120° C. with a slope of 2.5° C/minute. The temperature is maintained at 120° C. for 12 hours. This operating mode makes it possible to obtain yellowish crystals in the form of $DMOF-1-NH_2$ rods. The mother liquor is allowed to decant, and the crystals are washed three times with 6 ml of DMF, and then three times with 6 ml of $CH_2Cl_2$ (Acros Organics, 99.99%). Next, the crystals are left in suspension in 10 ml of $CH_2Cl_2$ for 3 days, with a renewal of solvent every 24 hours. Finally, the crystals are dried under vacuum at ambient temperature for one night. 300 mg of DMOF-1-NH$_2$ is thus obtained or a yield of 35% based on the initial Zn(NO$_3$)$_2$.4H$_2$O.

Said DMOF-1-NH$_2$ crystallized hybrid solid is analyzed by X-ray diffraction, by Fourier Transform Infrared spectroscopy, and by nuclear magnetic resonance of hydrogen ($^1$H NMR).

The X-ray diffraction analysis reveals that said solid that is obtained in Example 1 is identified as consisting of DMOF-1-NH$_2$ solid: the diffractogram that is implemented on said solid is identical to the one that is presented in *Inorganic Chemistry*, 2009, 48, 300.

The FT-IR analysis reveals the presence of the —NH$_2$ amino group in the DMOF-1-NH$_2$ IR (KBr pellet) solid, ν (cm$^{-1}$): 3454, 3344, 2958, 1632, 1666, 1577, 1435, 1376, 1256, 1056, 833, 810, 772, 704, 661, 593. The bands at 3454 and 3344 cm$^{-1}$ are attributed to the amine group.

The $^1$H-NMR analysis is implemented on a sample of the DMOF-1-NH$_2$ solid, after total digestion and dissolution of the sample in a DCl/D$_2$O/DMSO-d$_6$ deuterated mixture according to the operating mode that is described in the literature (Z. Q. Wang, S. M. Cohen, *Journal of the American Society*, 2007, 129, 12368-12369): 10 mg of DMOF-1-NH$_2$ hybrid solid is digested and dissolved in 1.5 ml of deuterated DMSO and 0.2 ml of a dilute DCl solution (prepared from a solution that contains 0.23 ml of DCl/D$_2$O at 35% and 1 ml of deuterated DMSO).

The $^1$H-NMR analysis also reveals the presence of the —NH$_2$ amino group in the DMOF-1-NH$_2$ solid. $^1$H NMR, 250 Hz, t.a, δ (ppm/(DCl/D$_2$O/DMSO-d$_6$)): 7.02 (d, 1H, J=8.3 Hz); 7.38 (s, 1H); 7.74 (d, 1H, J=8.3 Hz), 3.52 (s, 6H, DABCO).

The $^1$H-NMR analysis also makes it possible to confirm the presence of the NH$_2$-bdc and DABCO ligands in a proportion such that the NH$_2$-bdc/DABCO molar ratio=2.

Example 2

Preparation of the DMOF-1-N$_3$ Solid by Post-Modification of the DMOF-1-NH$_2$ Hybrid Solid 80 mg (0.27 mmol equivalent of —NH$_2$) of dried DMOF-1-NH$_2$ solid, obtained at the end of the process that is illustrated in Example 1, is placed in a flask (10 ml capacity) with 3 ml (37 mmol) of THF, 0.217 ml (1.84 mmol) of tBuONO (Aldrich), and 0.199 ml (1.508 mmol) of TMS-N$_3$ (Aldrich). After 12 hours of reaction at ambient temperature, the solid is filtered and then washed three times with 6 ml of THF (Carlo Erba), and then three times with 6 ml of CH$_2$Cl$_2$ before being dried under vacuum at ambient temperature.

The solid that is obtained has been analyzed by X-ray diffraction and identified as consisting of DMOF-1-N$_3$ crystallized hybrid solid: the diffractogram that is implemented on the DMOF-1-N$_3$ solid is the one that is provided by FIG. 1. The analysis that is implemented on the DMOF-1-N$_3$ crystallized hybrid solid by XRD demonstrates that the post-modification treatment that makes it possible to substitute the —NH$_2$ amino group by the —N$_3$ azide group does not affect the structure and the crystallinity of the solid.

The FT-IR analysis reveals the presence of the —N$_3$ azide group on each of the terephthalate ligands in the DMOF-1-N$_3$ solid. The spectrum that is obtained by FT-IR has a characteristic band of the azide group at 2123 cm$^{-1}$. The bands at 3454 and 3344 cm$^{-1}$ that correspond to the —NH$_2$ group have disappeared.

The $^1$H-NMR analysis is implemented on a sample of the DMOF-1-N$_3$ hybrid solid, after total digestion and dissolution of the sample in a DCl/D$_2$O/DMSO-d$_6$ deuterated mixture according to an operating mode that is described in the literature (Z. Q. Wang, S. M. Cohen, *Journal of the American Chemical Society*, 2007, 129, 12368-12369): 10 mg of DMOF-1-N$_3$ hybrid solid is digested and dissolved in 1.5 ml of deuterated DMSO and 0.2 ml of a dilute DCl solution (prepared from a solution that contains 0.23 ml of DCl/D$_2$O at 35% and 1 ml of deuterated DMSO).

The $^1$H-NMR analysis confirms the presence of the N$_3$ azide group in the aromatic cycle of the deprotonated terephthalic ligand. $^1$H NMR, 250 Hz, t.a, δ (ppm/(DCl/D$_2$O/DMSO-d$_6$)): δ=7.74-7.85 ppm, m, 3H, ArH. The 3 protons that lead to the detection of the multiplet correspond to 3 protons that are carried by the aromatic cycle of the 2-azido-terephthalate (N$_3$-bdc) ligand.

The comparison of the IR and $^1$H-NMR spectra that are obtained for the DMOF-1-NH$_2$ solid and for the DMOF-1-N$_3$ solid demonstrates the effectiveness of said post-modification treatment, the comparison of $^1$H-NMR spectra obtained for the DMOF-1-NH$_2$ solid and for the DMOF-1-N$_3$ solid that make it possible to estimate at 98% the rate of modification of the amino groups into N$_3$ azide groups, by quantifying the decrease of the relative area of the signals of the DMOF-1-NH$_2$ compound relative to those of the DMOF-1-N$_3$ compound.

The invention claims is:

1. A crystallized hybrid solid having a three-dimensional organic-inorganic matrix represented by the formula:

DMOF-1-N$_3$, which comprises an inorganic network of zinc metal centers connected to each other by an organic ligand represented by the formula:

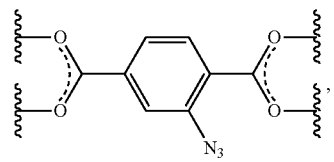 [SMILES: *OC(O*)c1ccc(C(O*)O*)c(N=[N+]=[N-])c1]

and an organic ligand represented by the formula:

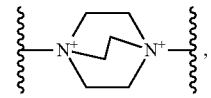

wherein the crystallized hybrid solid has a chemical composition having the following base pattern:

Zn$_2$(—O$_2$C—C$_6$H$_3$—N$_3$—CO$_2$—)$_2$(C$_6$H$_{12}$N$_2$), and further wherein the crystallized hybrid solid is characterized by an X-ray diffraction diagram comprising at least the lines in the table below:

| 2 Thêta (°) | d$_{hkl}$ (Å) | I/I$_0$ |
| --- | --- | --- |
| 8.152 | 10.837643 | F |
| 9.19 | 9.615264 | mf |
| 11.538 | 7.663371 | mf |
| 12.296 | 7.192531 | mf |

-continued

| 2 Thêta (°) | $d_{hkl}$ (Å) | $I/I_0$ |
|---|---|---|
| 14.77 | 5.992845 | ff |
| 16.345 | 5.418821 | FF |
| 18.29 | 4.846741 | f |
| 18.44 | 4.807632 | ff |
| 18.782 | 4.720763 | f |
| 20.19 | 4.394638 | ff |
| 20.504 | 4.327992 | ff |
| 21.806 | 4.072553 | ff |
| 23.195 | 3.831685 | ff |
| 24.623 | 3.612547 | f |
| 24.737 | 3.596266 | ff |
| 24.996 | 3.559468 | ff |
| 25.978 | 3.427163 | ff |
| 26.086 | 3.413252 | ff |
| 26.333 | 3.381744 | ff |
| 27.609 | 3.228232 | ff |
| 27.813 | 3.205088 | ff |
| 29.029 | 3.0735 | f |
| 29.698 | 3.005821 | ff |
| 29.793 | 2.996423 | ff |
| 30.201 | 2.956894 | ff |
| 30.938 | 2.888069 | ff |
| 31.15 | 2.868907 | ff |
| 32.046 | 2.790679 | ff |
| 32.428 | 2.758663 | ff |
| 33.035 | 2.709411 | ff |
| 33.492 | 2.673413 | ff |
| 34.082 | 2.628514 | ff |
| 34.36 | 2.607855 | ff |
| 35.102 | 2.554457 | ff |
| 35.184 | 2.548681 | ff |
| 35.373 | 2.535482 | ff |
| 36.361 | 2.468819 | ff |
| 36.52 | 2.458421 | ff, | where
FF = very high;
F = high;
m = medium;
mf = medium low;
f = low;
ff = very low,
with the relative intensity $I/I_0$ being provided relative to a relative intensity scale where a value of 100 is assigned to the most intense line of the X-ray diffraction diagram: ff < 15; 15 ≤ f < 30; 30 ≤ mf < 50; 50 ≤ m < 65; 65 ≤ F < 85; and FF ≥ 85."

2. The crystallized hybrid solid according to claim 1, wherein the crystallized hybrid solid has a crystalline structure identical to a DMOF-1-NH$_2$ crystallized hybrid solid, with the exception that the —NH$_2$ groups of the DMOF-1-NH$_2$ crystallized hybrid solid are replaced by —N$_3$ groups.

3. The crystallized hybrid solid according to claim 1, wherein each zinc atom is surrounded by four oxygen atoms obtained from four equatorial N$_3$-benzene-1,4-dicarboxylate ligands and a nitrogen atom obtained from an apical 1,4-diazabicyclo[2.2.2]octane ligand.

4. A process for the preparation of a crystallized hybrid solid according to claim 1, comprising:
i) reacting a crystallized hybrid solid represented by the formula:

DMOF-1-NH$_2$, with a compound represented by the formula:

R-NO$_2$, wherein R is selected from the group consisting of sodium and tert-butyl, and a compound represented by the formula:

Q-N$_3$, wherein Q is selected from the group consisting of sodium, trimethylsilyl, toluenesulfonyl and trifluoromethanesulfonyl,
in the presence of a polar solvent, S, at a temperature between 0° C. and 100° C. for a period between 1 and 24 hours, and further
wherein the reaction mixture has the following molar composition:

1 DMOF-1-NH$_2$:3-12 R—NO$_2$:1-9 Q-N$_3$:100-400 S; and ii) drying the crystallized hybrid solid represented by the formula:

DMOF-1-N$_3$.

5. The process according to claim 4, wherein the crystallized hybrid solid represented by the formula, DMOF-1-NH$_2$, is dried prior to addition to the polar solvent, S.

6. The process according to claim 4, wherein Q in the compound represented by the formula, Q-N$_3$, is trimethylsilyl.

7. The process according to claim 4, wherein R in the compound represented by the formula, R—NO$_2$, is tert-butyl.

8. The process according to claim 4, wherein the polar solvent, S, is selected from the group consisting of tetrahydrofuran and acetonitrile.

9. The process according to claim 4, wherein the reaction mixture has the following molar composition:

1 DMOF-1-NH$_2$:5-7 R—NO$_2$:5-8 Q-N$_3$:100-200 S.

10. The process according to claim 4, wherein the reaction is performed at ambient temperature.

11. The process according to claim 4, wherein the reaction is performed for a period between 5 and 15 hours.

\* \* \* \* \*